United States Patent [19]
Hillstead

[11] Patent Number: 5,135,536
[45] Date of Patent: Aug. 4, 1992

[54] ENDOVASCULAR STENT AND METHOD

[75] Inventor: Richard A. Hillstead, Miami, Fla.

[73] Assignee: Cordis Corporation, Miami Lakes, Fla.

[21] Appl. No.: 650,699

[22] Filed: Feb. 5, 1991

[51] Int. Cl.$^5$ .................. A61M 29/00; A61F 2/06; A61F 2/04
[52] U.S. Cl. ........................... 606/195; 623/1; 623/12
[58] Field of Search ............ 606/108, 191–195; 623/1, 12; 604/96

[56] References Cited

U.S. PATENT DOCUMENTS

| | | | |
|---|---|---|---|
| 4,140,126 | 2/1979 | Choudhury | 606/194 |
| 4,503,569 | 3/1985 | Dotter | 623/1 |
| 4,733,665 | 3/1988 | Palmaz | 606/191 X |
| 4,830,003 | 5/1989 | Wolff et al. | 606/191 |
| 4,856,516 | 8/1989 | Hillstead | 606/194 |
| 5,019,090 | 5/1991 | Pinchuk | 606/194 |

*Primary Examiner*—Ronald Frinks
*Attorney, Agent, or Firm*—Watts, Hoffmann, Fisher & Heinke Co.

[57] ABSTRACT

A stent for reinforcing a vessel wall is disclosed. The stent is constructed from a single elongated wire. The wire is first bent into a series of tight bends. The wire is then rolled around a mandrel to create junctions of wire which are permanently adhered. The completed stent forms a cylindrical form which can be expanded from an initial diameter to a larger implanted diameter by application of a radially outward force from a balloon catheter or the like.

24 Claims, 4 Drawing Sheets

ENDOVASCULAR STENT AND METHOD

TECHNICAL FIELD

The present invention relates to an endoprosthesis device for implantation within a body vessel, typically a blood vessel.

BACKGROUND ART

A type of endoprosthesis device, commonly referred to as a stent, is placed or implanted within a blood vessel for treating stenoses, strictures, or aneurysms in the blood vessel. These devices are implanted within the vascular system to reinforce collapsing, partially occluded, weakened, or abnormally dilated sections of the blood vessel. Stents also have been successfully implanted in the urinary tract or the bileducts to reinforce those body vessels.

One common procedure for implanting the endoprosthesis or stent is to first open the region of the vessel with a balloon catheter and then place the stent in a position that bridges the weakened portion of the vessel.

Prior art patents refer to the construction and design of both the stent as well as the apparatus for positioning the stent within the vessel. One representative patent is U.S. Pat. No. 4,140,126 to Chaudhury which issued Feb. 20, 1979. This patent discloses a technique for positioning an elongated cylindrical stent at a region of an aneurysm to avoid catastrophic failure of the blood vessel wall. The '126 patent discloses a cylinder that expands to its implanted configuration after insertion with the aid of a catheter.

A second prior art patent to Dotter, U.S. Pat. No. 4,503,569 which issued Mar. 12, 1985 discloses a spring stent which expands to an implanted configuration with a change in temperature. The spring stent is implanted in a coiled orientation and heated to cause the spring to expand.

U.S. Pat. No. 4,733,665 to Palmaz which issued Mar. 29, 1988 discloses a number of stent configurations for implantation with the aid of a catheter. The catheter includes a mechanism for mounting and retaining the vascular prosthesis or stent, preferably on an inflatable portion of the catheter. The stent is implanted by positioning it within the blood vessel and monitoring its position on a viewing monitor. Once the stent is properly positioned, the catheter is expanded and the stent separated from the catheter body. The catheter can then be withdrawn from the subject, leaving the stent in place within the blood vessel.

U.S. Pat. No. 4,856,516 to Hillstead entitled "Endovascular Stent Apparatus and Method" discloses a radially expandable stent for placement within a subject vessel. The stent is constructed from an elongated wire that is bent into a series of tight bends which are wrapped around a mandrel to form a series of loops. These loops are then interconnected by half hitch junctions. The disclosure of the '516 patent to Hillstead is incorporated herein by reference.

U.S. patent application Ser. No. 240,000 now U.S. Pat. No. 5,019,090, entitled "Radially Expandable Endoprosthesis and the Like" discloses a generally cylindrical stent formed from a wire that is bent into a series of tight bends and then spirally wound about a cylindrical mandrel to form the stent. If a radially outward force is applied to the stent the sharp bends in the wire tend to straighten and the stent diameter enlarges. One technique for implanting this stent uses a deflated balloon catheter to position the stent within a vessel. Once the stent is properly positioned the balloon is inflated to press the stent against the inner wall linings of the vessel. The balloon is then deflated and withdrawn from the vessel, leaving the stent in place.

DISCLOSURE OF THE INVENTION

The present invention concerns a stent for placement within a subject. The invention utilizes an elongated flexible filament bent into a series of tight bends extending along a series of transverse portions of the filament. The filament is then rolled around a mandrel to give the stent its cylindrical shape. The transverse portions meet along a series of junctions which are substantially aligned. These junctions are then permanently adhered to prevent unrolling of the completed stent. A backbone is formed by the adhering of these junctions in the stent thereby providing structure and strength.

A feature of the invention allows for the omission of one or more stent segments thereby creating gaps to accommodate branching or crossing vessels within the subject vessel.

The completed stent is of a sturdy, yet flexible nature. It is capable of being easily placed within a subject vessel in a reduced diameter configuration that fits within a guide catheter. When properly positioned, the stent can be expanded using a balloon catheter. The implanted stent provides support and reinforcement to the subject vessel as it heals.

These and other objects of the invention will be better understood from the following description of the invention which is described in conjunction with the accompanying drawings.

DETAILED DESCRIPTION

Figure 1:
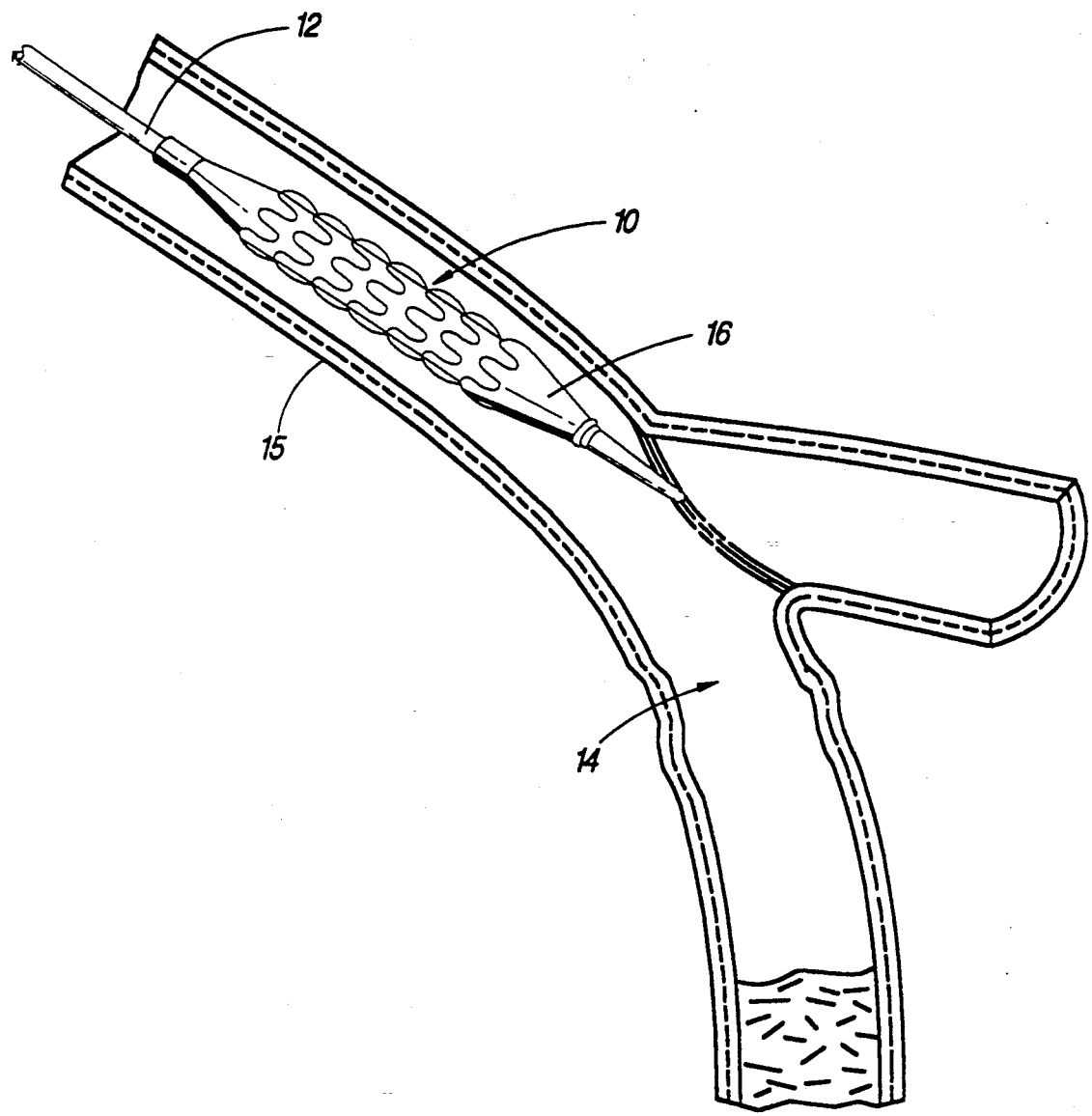
FIG. 1 is a schematic depiction of a stent carried by a balloon catheter as the stent is routed to an implantation position.

Turning now to the drawings, FIG. 1 shows a generally cylindrical stent 10 mounted to a balloon catheter 12 which is being routed through a patient's cardiovascular system to a weakened region 14 of a blood vessel 15. The balloon catheter 12 is of a conventional design and includes a catheter portion that defines a passageway extending from the catheter's proximal to distal end. The passageway allows fluid to be routed to a balloon 16 near the catheter's distal tip to inflate the balloon. As the balloon inflates it exerts a radially outward force against the stent 10 causing the stent to expand into contact with an inner wall of the blood vessel 15.

To release the stent within the blood vessel 15, the balloon 16 is then deflated causing the balloon and stent to separate. The stent 10 is then fixed within the blood vessel 15 due to frictional engagement between the stent and the inner wall lining of the blood vessel 15. The deflated balloon 16 can then be freely withdrawn from the stent. As this procedure is being accomplished, the attending physician can monitor progress of the stent implantation on a viewing monitor to determine the adequacy of the placement.

Figure 2:
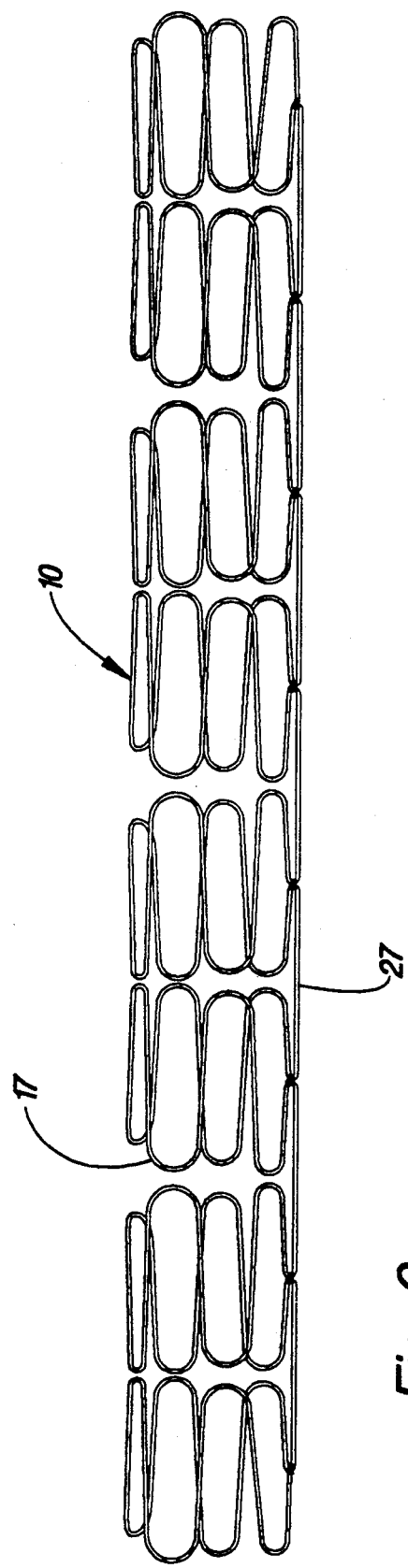
FIG. 2 is an elevation view of a stent embodying this invention.
Figure 3:
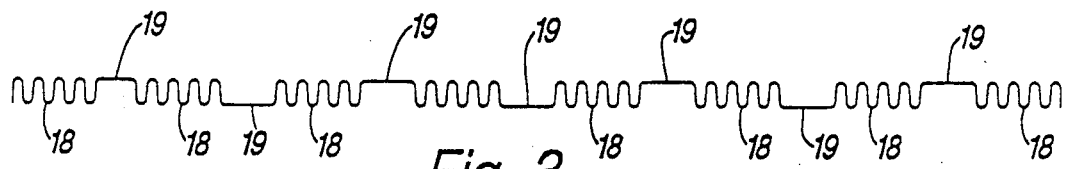
FIG. 3 is a plan view of a filament having a series of tight bends at regular intervals along its length.
Figure 4:
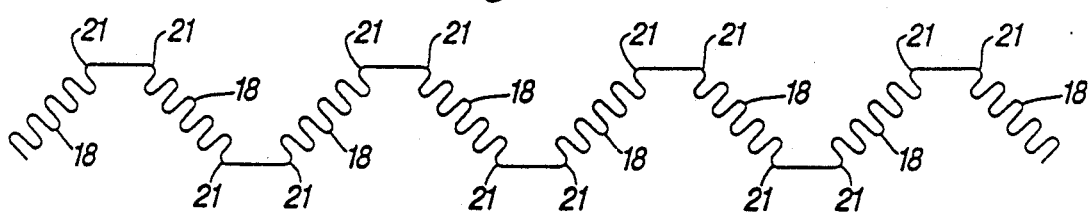
FIG. 4 is a plan view of the FIG. 3 filament indicating a manner in which the filament is bent during fabrication of the stent.
Figure 5:
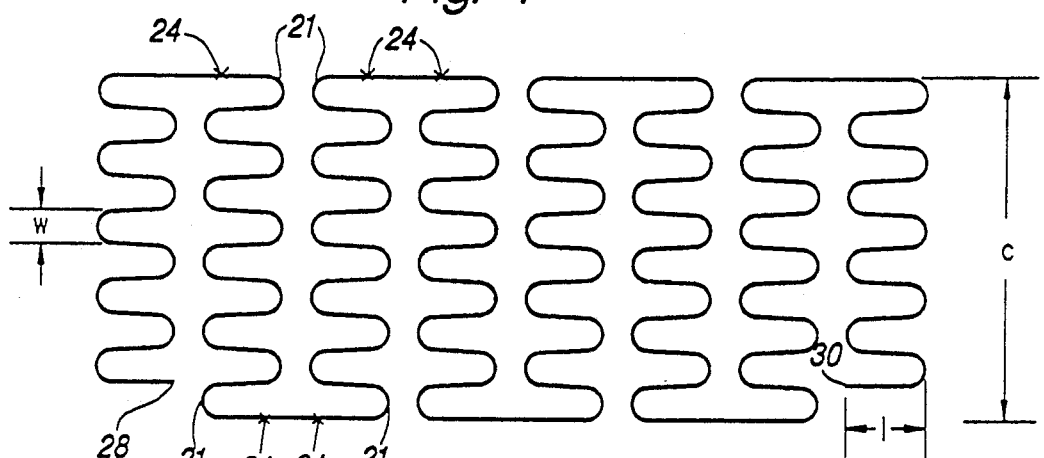
FIG. 5 is a plan view of a planar form fabricated from the filament depicted in FIGS. 3 and 4.
Figure 6:
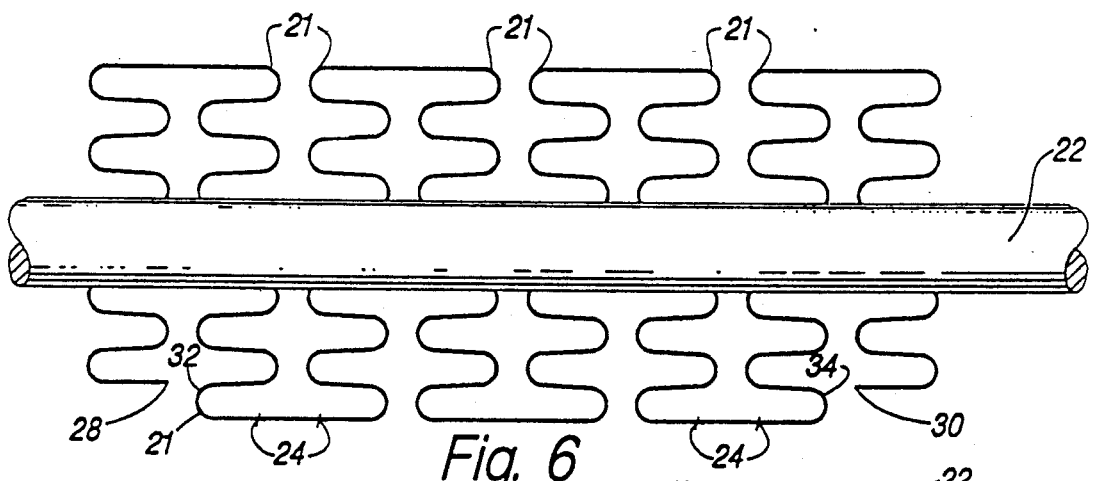
FIG. 6 is a plan view of the planar form of the filament indicated in FIG. 5 with a mandrel for wrapping of the filament.
Figure 7:
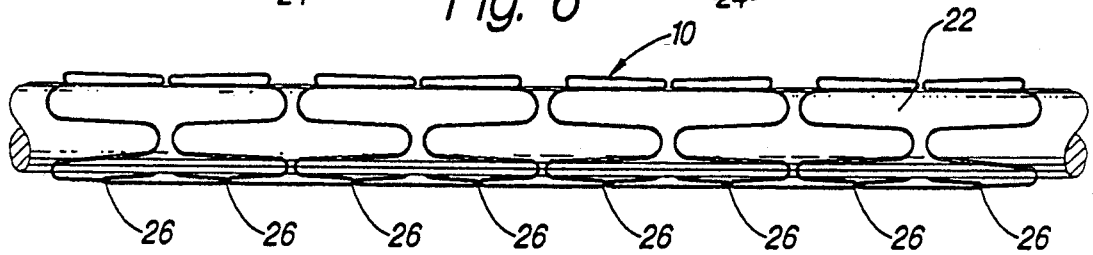
FIG. 7 is a plan view of the filament indicated in FIG. 6 wrapped around the mandrel; and, FIG. 8 is an elevation view of a stent embodying this invention with a section removed to create a gap to accommodate branching vessels.

FIG. 2 depicts a stent 10 built from an elongated filament 17, typically a wire, in accordance with this invention. As seen in FIGS. 3 and 4, series of bends 18 are formed at regular intervals. Each series of bends 18 is spaced from an adjacent series by a straight segment 19. Bending both ends 21 of each straight segment 19 forms a generally planar form defined by a series of transverse portions having a width C equal to the circumference of the stent 10 (See FIG. 5). The form is then rolled around a mandrel 22 as shown in FIGS. 6 and 7. After it is rolled, the stent 10 has a cylindrical shape. Each end 21 of a straight segment 19 is closely adjacent to a location 24 of a different straight segment 19. The locations 24 are indicated in FIGS. 5 and 6.

Filament portions at the each end 21 and location 24 are permanently adhered together to form junctions 26 to prevent the unrolling of the stent 10 upon the removal of the mandrel 22. The junctions 26 can be adhered and formed through means of welding, soldering, tying or suturing. In the situation where the junctions are tied or sutured, the material used for the tying or suturing could be bio-degradable and in fact would be preferred. The junctions 26 are generally aligned to form a backbone 27. End portions 28, 30 are hooked to a closely adjacent bend 18 at locations 32, 34 respectively. The end portions could also be permanently adhered to their respective bends.

A preferred stent 10 is constructed using tantalum wire having a diameter of 5 thousandths of an inch. Before they are straightened by the balloon 16, the bends have typical widths w of 0.048±0.002 inch and lengths l of 0.042±0.003 inch (FIG. 5).

A feature of the stent 10 constructed in accordance with the present invention is its ability to expand as outward pressure is applied to its length by the balloon 16. This ability stems from a combination of the factors as previously discussed above. The main factor, however, is the series of sharp bends 18 applied to the filament 17 from which the stent 10 are constructed.

Figure 8:
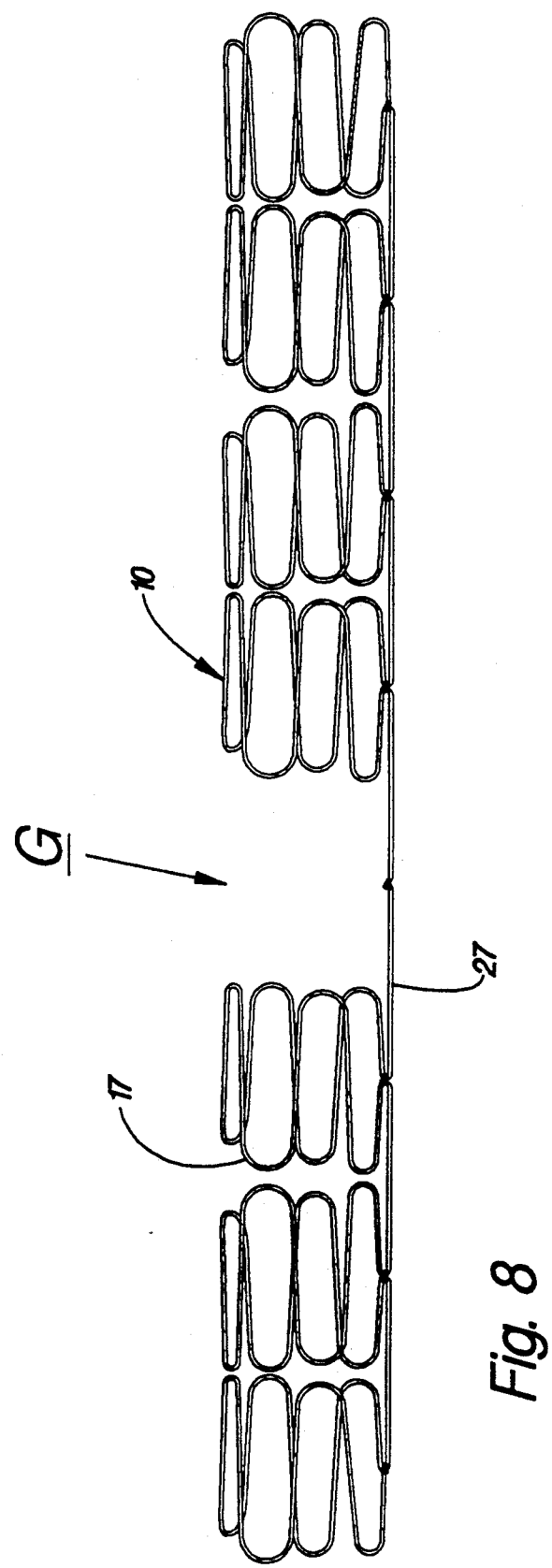

One additional feature of the proposed construction is the omission of one or more segments along length portions of the stent 10 which defines a gap G (illustrated in FIG. 8). This construction would accommodate, for example, the use of the stent wherein side or branch vessels are encountered and would allow unimpeded fluid flow to those side or branching vessels through judicious placement of the stent.

This stent embodiment have been described with a degree of particularity. It is the intent that the invention include all alterations from this embodiment falling within the spirit or scope of the appended claims.

I claim:

1. A stent for placement within a subject vessel comprising a support dimensioned to fit within an interior of said subject vessel including an elongated flexible filament having a plurality of transverse portions each defined by a series of at least three bends, said transverse portions being rolled to create a cylindrical shape having closely spaced filament portions permanently adhered together to form junctions that prevent unrolling of said filament.

2. The stent of claim 1 wherein said junctions are welded.

3. The stent of claim 1 wherein said junctions are soldered.

4. The stent of claim 1 wherein said stent is radially expandable from a first outer diameter which fits within said vessel to a second increased diameter which contacts an inner wall surface of said vessel to reinforce said inner wall.

5. The stent of claim 1 wherein an inner diameter of said stent is dimensioned to frictionally engage a noninflated balloon catheter and be carried by said noninflated catheter into a blood vessel.

6. The stent of claim 1 wherein said junctions are regularly spaced along a length portion of said stent and are permanently adhered and aligned along said length portion of said stent to form a relatively straight backbone to said stent.

7. The stent of claim 6 wherein gaps are left along said length portion of said stent to accommodate branches in said vessel so that said stent does not block off fluid flow through said branches.

8. A stent for placement within a subject vessel comprising a support dimensioned to fit within an interior of said subject vessel including an elongated flexible filament defining a series of bends extending along a series of transverse portions that are rolled to create a cylindrical shape having closely spaced filament portions permanently adhered together by tying or suturing to form junctions that prevent unrolling of said filament.

9. A stent for placement within a subject vessel comprising a support dimensioned to fit within an interior of said subject vessel including an elongated flexible filament defining a series of bends extending along a series of transverse portions that are rolled to create a cylindrical shape having closely spaced filament portions adhered together by tying or suturing with a biodegradable material to form junctions that prevent unrolling of said filament.

10. A stent for placement within a subject vessel comprising a support dimensioned to fit within an interior of said subject vessel including an elongated flexible filament defining a series of transverse portions, each transverse portion defining a series of at least three bends, said transverse portions being rolled to create a cylindrical shape having closely spaced filament portions to form junctions that prevent unrolling of said filament, wherein:

a) said junctions are regularly spaced along a length portion of said stent and are permanently adhered together and aligned along said length portion of said stent to form a relatively straight backbone to said stent;

b) said stent is radially expandable from a first outer diameter which fits within said vessel to a second increased diameter which contacts an inner wall surface of said vessel to reinforce said inner wall; and, c) an inner diameter of said stent is dimensioned to frictionally engage a non-inflated balloon catheter and be carried by said non-inflated catheter into a blood vessel.

11. The stent of claim 10 wherein said junctions are welded.

12. The stent of claim 10 wherein said junctions are soldered.

13. The stent of claim 10 wherein gaps are left along said length portion of said stent to accommodate branches in said vessel so that said stent does not block off fluid flow through said branches.

14. A stent for placement within a subject vessel comprising a support dimensioned to fit within an interior of said subject vessel including an elongated flexible filament defining a series of bends extending along a series of transverse portions that are rolled to create a cylindrical shape having closely spaced filament portions to form junctions that prevent unrolling of said filament, wherein:
 a) said junctions are regularly spaced along a length portion of said stent and are permanently adhered together by tying or suturing and are aligned along said length portion of said stent to form a relatively straight backbone to said stent;
 b) said stent is radially expandable from a first outer diameter which fits within said vessel to a second increased diameter which contacts an inner wall surface of said vessel to reinforce said inner wall; and,
 c) an inner diameter of said stent is dimensioned to frictionally engage a non-inflated balloon catheter and be carried by said non-inflated catheter into a blood vessel.

15. A stent for placement within a subject vessel comprising a support dimensioned to fit within an interior of said subject vessel including an elongated flexible filament defining a series of bends extending along a series of transverse portions that are rolled to create a cylindrical shape having closely spaced filament portions to form junctions that prevent unrolling of said filament, wherein:
 a) said junctions are regularly spaced along a length portion of said stent and are adhered together by tying or suturing with a biodegradable material and are aligned along said length portion of said stent to form a relatively straight backbone to said stent;
 b) said stent is radially expandable from a first outer diameter which fits within said vessel to a second increased diameter which contacts an inner wall surface of said vessel to reinforce said inner wall; and,
 c) an inner diameter of said stent is dimensioned to frictionally engage a non-inflated balloon catheter and be carried by said non-inflated catheter into a blood vessel.

16. A method of fabricating a generally cylindrical stent, said method comprising:
 a) bending an elongated filament into a plurality of series of relatively tight bends;
 b) bending said filament into a plurality of transverse portions, each transverse portion having at least three of the relatively tight bends;
 c) providing a cylindrical mandrel of a dimension smaller than an inner diameter of a vessel into which said stent is to be inserted;
 d) rolling said filament around said mandrel such that ends of said transverse portions meet locations of adjacent filament portions thereby creating said cylindrical shape;
 e) permanently adhering said ends and locations to create junctions of filament; and
 f) removing said filament from said mandrel to define a throughpassage for fluid passage through said stent in a region previously occupied by said mandrel.

17. The method of claim 16 wherein said junctions are permanently adhered by welding.

18. The method of claim 16 wherein said junctions are permanently adhered by soldering.

19. The method of claim 16 wherein subsequent to said removal of said stent from said mandrel, one or more transverse portions are removed from said stent to create gaps to accommodate branching vessels and allow unimpeded fluid flow to said branching vessels after said stent is positioned within said vessel.

20. A method of fabricating a generally cylindrical stent, said method comprising:
 a) bending an elongated filament into a plurality of series of relatively tight bends;
 b) providing a cylindrical mandrel of a dimension smaller than an inner diameter of a vessel into which said stent is to be inserted;
 c) rolling said filament around said mandrel to create junctions of filament thereby creating said cylindrical shape;
 d) permanently adhering said junctions of filament;
 e) removing said filament from said mandrel to define a throughpassage for fluid passage through said stent in a region previously occupied by said mandrel; and,
 f) removing one or more sections of filament from said stent to create gaps to accommodate branching vessels and allow unimpeded fluid flow to said branching vessels after said stent is positioned within said vessel.

21. A method of fabricating a generally cylindrical stent, said method comprising:
 a) bending an elongated filament into a plurality of series of relatively tight bends;
 b) providing a cylindrical mandrel of a dimension smaller than an inner diameter of a vessel into which said stent is to be inserted;
 c) rolling said filament around said mandrel to create junctions of filaments thereby creating said cylindrical shape;
 d) permanently adhering said junctions of filament by tying or suturing;
 e) removing said filament from said mandrel to define a throughpassage for fluid passage through said stent in a region previously occupied by said mandrel.

22. A method of fabricating a generally cylindrical stent, said method comprising:
 a) bending an elongated filament into a plurality of series of relatively tight bends;
 b) providing a cylindrical mandrel of a dimension smaller than an inner diameter of a vessel into which said stent is to be inserted;
 c) rolling said filament around said mandrel to create junctions of filament thereby creating said cylindrical shape;
 d) adhering said junctions of filament by tying or suturing with a biodegradable material;
 e) removing said filament from said mandrel to define a throughpassage for fluid passage through said stent in a region previously occupied by said mandrel.

23. A stent for reinforcing a vessel within a subject comprising a cylindrical support dimensioned to fit within an interior of said vessel including:
   a) an elongated filament bent to define segments of relatively tightly spaced bends which form a plurality of loops spaced along an axial dimension of the stent connected by a plurality of generally straight wire segments; and,
   b) means for connecting together different straight wire segments;

wherein said stent is radially expandable from a first outer diameter which fits within said vessel to a second increased diameter which contacts an inner wall surface of said vessel to reinforce said inner wall.

24. A stent for reinforcing a vessel comprising a wire having alternating bent and straight portions wherein the bent portions form cicumferential loops about a stent throughpassage to bring alternate straight line portions into contact at aligned locations along a length of the stent, and means for connecting at least some of said straight portion locations together.

* * * * *